United States Patent
Steenhoek et al.

(10) Patent No.: US 7,027,147 B2
(45) Date of Patent: *Apr. 11, 2006

(54) METHOD AND APPARATUS FOR MEASURING THE COLOR PROPERTIES OF FLUIDS

(75) Inventors: Larry Eugene Steenhoek, Wilmington, DE (US); Anthony Joseph Martino, West Chester, PA (US)

(73) Assignee: E. I. duPont de Nemours and Company, Wilmington, DE (US)

( * ) Notice: Subject to any disclaimer, the term of this patent is extended or adjusted under 35 U.S.C. 154(b) by 151 days.

This patent is subject to a terminal disclaimer.

(21) Appl. No.: 10/097,999

(22) Filed: Mar. 13, 2002

(65) Prior Publication Data

US 2002/0131043 A1    Sep. 19, 2002

Related U.S. Application Data

(60) Provisional application No. 60/276,991, filed on Mar. 19, 2001.

(51) Int. Cl.
G01N 1/10    (2006.01)

(52) U.S. Cl. .................. 356/246; 356/410
(58) Field of Classification Search ........... 356/246, 356/236, 326, 319, 410, 409, 416, 402, 436, 356/331

See application file for complete search history.

(56) References Cited

U.S. PATENT DOCUMENTS 2,819,402 A * 1/1958 Bresky et al. .............. 250/428
3,740,156 A * 6/1973 Heigl et al. ................. 356/433
3,999,867 A * 12/1976 Stabell ....................... 356/246
4,152,073 A * 5/1979 Zimmerman ................. 356/436
4,192,614 A * 3/1980 deMey, et al. .............. 356/410
4,403,866 A   9/1983 Falcoff et al.
4,425,235 A * 1/1984 Cornell et al. .............. 210/516
4,511,251 A   4/1985 Falcoff et al.
4,528,657 A * 7/1985 Meehan ....................... 378/47
4,582,657 A * 4/1986 Shibata et al. ............. 264/40.6
4,786,171 A * 11/1988 LeFebre et al. ............. 356/326
4,887,217 A   12/1989 Sherman et al.
4,890,920 A   1/1990 Niziolek et al.
4,936,685 A   6/1990 Taylor et al.
4,995,727 A * 2/1991 Kawagoe et al. ............ 356/402
6,288,783 B1   9/2001 Auad
6,507,397 B1 * 1/2003 Nishio et al. ............... 356/319
6,573,988 B1 * 6/2003 Thomsen et al. ........... 356/246
2002/0149773 A1 * 10/2002 Martino et al. ............. 356/436

FOREIGN PATENT DOCUMENTS

BR    PI9800361-5    2/1998
DE    25 25 701 A1   12/1976

(Continued)

*Primary Examiner*—Layla G. Lauchman
(74) *Attorney, Agent, or Firm*—Chyrrea J. Sebree

(57) ABSTRACT

An apparatus for inspection of fluids, particularly dispersions and tints, having a fluid analysis cell with a cavity enclosed by two light transmitting windows and having a spacer member fixedly positioned therebetween which provides a fluid analysis chamber of fixed pathlength where fluid flows by the windows and wherein the flow is laminar and at a uniform shear to provide accurate color measurements. The apparatus is particularly useful in the manufacture of dispersions and tints used in the manufacture of paints, so that the color of material being made can be accurately matched to a standard color in the wet state with confidence that the color will match in the dry state.

13 Claims, 4 Drawing Sheets

FOREIGN PATENT DOCUMENTS

| | | |
|---|---|---|
| DE | 240 075 A1 | 10/1986 |
| FR | 2 594 131 A1 | 8/1987 |
| GB | 1 589 705 | 5/1981 |
| GB | 2355524 A * | 4/2001 |
| SU | 364877 | 11/1973 |
| WO | WO99/48602 A1 | 9/1999 |

* cited by examiner

METHOD AND APPARATUS FOR MEASURING THE COLOR PROPERTIES OF FLUIDS

CROSS-REFERENCE TO RELATED APPLICATION

This application claims priority under 35 U.S.C. §119 from U.S. Provisional Application Ser. No. 60/276,991 (filed Mar. 19, 2001), which is incorporated by reference herein for all purposes as if fully set forth.

BACKGROUND OF THE INVENTION

This invention relates to a method of and apparatus for the inspection of fluids. In particular, the invention relates to an improved apparatus for measuring the color properties, in transmission, of fluids, such as pigment dispersions and tints flowing through the apparatus.

Pigment dispersions and tints are widely used nowadays in formulating high performance coating compositions used in particular for exterior finishes for automobiles and trucks.

In the manufacture of such dispersions and tints, one problem is to measure the color and strength of the material as it is being made, so that adjustments can be quickly made to bring this material within acceptable color tolerance values. Color measurements nowadays are carried out by a manual process, which involves taking an aliquot of the material, blending it with a standard white or black paint, spraying out the blends as a coating onto panels, baking and drying the panels, and then measuring one or more color properties of the dried coating using a calorimeter or spectrophotometer against a standard. Adjustments are then made to the batch until the color parameters match those of the standard.

Color measurements by this method are very time consuming because of sample preparation and drying times. Also, this procedure may have to be repeated numerous times before the desired color property is achieved. Another problem which arises with this procedure is that the accuracy of the test is dependent on the color and strength stability of the standard white or black paints. Even with careful control, these standards tend to vary from batch to batch and also tend to flocculate or settle in time, leading to poor test repeatability and making it very difficult to accurately analyze the color and strength of the batch as it is being made.

The aim within the industry for some time has been to measure the color properties of these fluids in a wet state and in a way which predicts the color of the fluid when applied and dried. The primary benefits are mainly associated with time savings although some are associated with the increased likelihood of an automated manufacturing process.

Conventional spectrophotometers, employing cuvette-type sample chambers, have been proposed to make such wet measurements by measuring a transmission spectrum of a wet transparent sample. Simply taking a sample of wet fluid and putting it in a glass cell and measuring its color properties generally leads to inconsistent results, mostly due to poor repeatability and operator variability. In addition, cell pathlengths in such spectrophotometers are, in general, too large for such measurements. Moreover, settling and flocculation can also occur, changing the color of the sample and producing erroneous results.

Another instrument, described in Batista et al. WO 98/16822, published Apr. 23, 1998, employing a variable pathlength fluid measurement cell to measure properties of fluids, including color, could be used for such measurements. However, this equipment possesses multiple moving parts which are part of the fluid path, which causes difficulty in cleaning, and are difficult to maintain. Another disadvantage is that the design is such that it requires a high volume of fluid sample to take proper readings.

Therefore, there is still a need to provide a method and apparatus for color measurement of wet fluids that: produces acceptably consistent results; does not require the spraying and blending with white or black standards and the production of a number of dry samples; cleans rapidly (within 1 or 2 minutes) so that the cycle time of the measurement is extremely small compared to process changes; and predicts with confidence that the wet readings will also match the standard in the dry.

In addition to the above features, there is also a need to provide a method and apparatus that automatically delivers sample to the analysis cell so that said apparatus could be easily connected to a process stream on-line for measurement and control of process color and strength; and is intrinsically safe, so that it can be placed on a plant floor in an environment wherein may be contained an explosive atmosphere.

SUMMARY OF THE INVENTION

An apparatus for inspection of fluids having the following components:

a fluid analysis cell having a cavity therein for measuring light transmittance of a sample;

an upper and lower light transmitting window enclosing opposite ends of the cavity;

a spacer fixedly positioned in said cavity between said upper and lower viewing windows providing a fluid chamber where fluid flows between said windows;

inlet and outlet channels connected in fluid communication with said fluid chamber to enable fluid to flow into and out of said fluid chamber, the flow of fluid through the chamber preferably being unidirectional laminar flow at uniform shear; and, a light source and a spectrophotometer, preferably a single beam spectrophotometer, associated with the cell to measure color parameters of the fluid passing through the viewing window by transmittance.

The inspection apparatus also preferably includes the following components:

a camera lens to interface with the spectrophotometer to gather light from diffuse as well as specular directions;

a purged explosion-proof enclosure for containing all electrical/electronic components, as well as the light source for the instrument;

an automatic pneumatically-controlled sample system for delivery of the sample to the fluid analysis chamber; and, an explosion-proof pump for high pressure delivery of cleaning solvent to the fluid analysis chamber for rapid cleaning of said chamber.

A method for measuring the color properties of a fluid using the above apparatus is also a part of this invention.

DETAILED DESCRIPTION OF THE PREFERRED EMBODIMENTS

In general, the apparatus of the invention can be used to inspect a wide variety of fluids (such as dispersions, tints, inks, paints, and etc.) but is designed particularly to measure the color properties of dispersions and tints that are used in the manufacture of high performance automotive coatings. The apparatus is specifically designed to measure the color properties of the fluids flowing through the apparatus using wet light transmittance measurements over the visible spectrum in a way that produces accurate instrumental readings.

Figure 1:
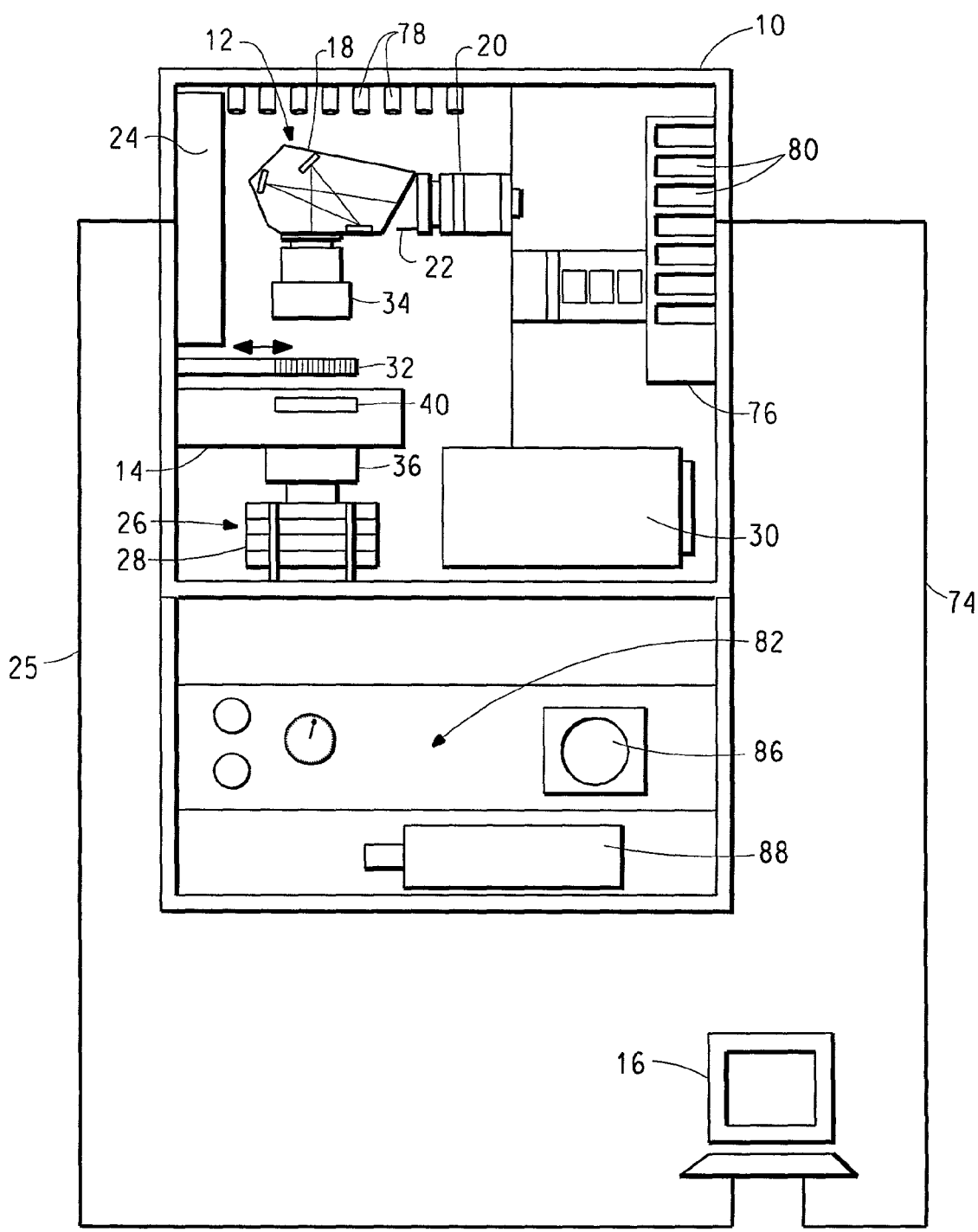
FIG. 1 is a front view of the apparatus in accordance with the invention.
Figure 2:
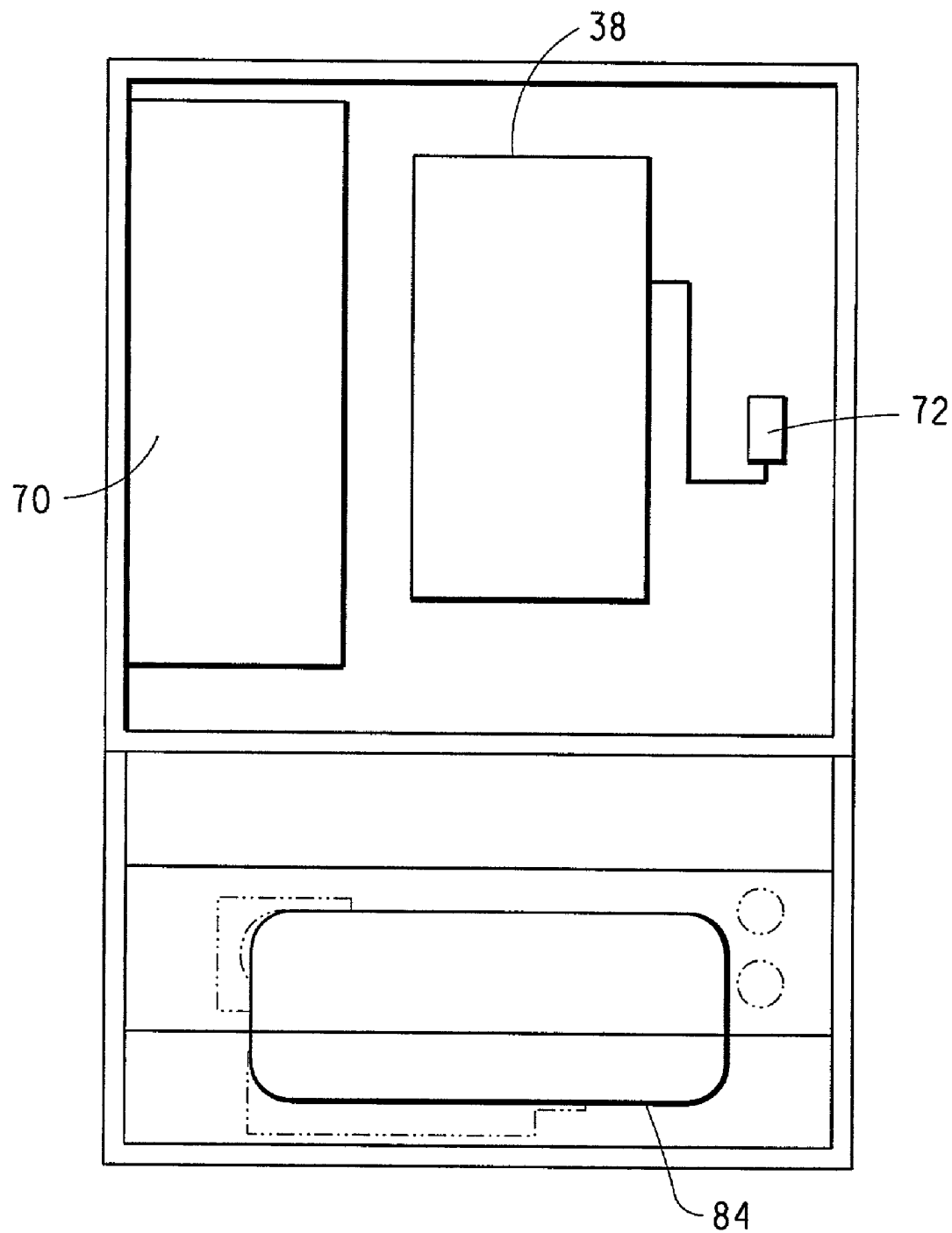
FIG. 2 is a rear view of the apparatus of FIG. 1.

Referring now to FIGS. 1 and 2 of the drawings, the apparatus according to the invention comprises a housing 10 which contains an optical unit 12, for providing a source of visible light to a fluid analysis unit 14 and for detecting the visible light emitted therefrom. Both the optical unit 12 and fluid analysis unit 14 are connected to a system control unit, preferably a computer, 16 for data acquisition, spectral analysis, and control of the functions of units 12 and 14.

The optical unit 12 preferably consists of a monochromator 18 and a photodiode array detector 20, together in essence comprising a single beam spectrophotometer, having a single input 22 for detecting light over the visible spectrum, from 400 nm to 700 nm, typically in 10 nm increments. The photodiode array is controlled by a controller unit 24 interfaced with the system control unit 16, preferably via an optical RS-232 interface contained therein utilizing a fiber optic cable 25. Light is provided to input 22 from a light source 26 preferably consisting of an incandescent halogen lamp (not shown), e.g., a tungsten halogen lamp, that emits light over a range of wavelengths from 400 to 700 nanometers (nm). The lamp is contained in a housing 28 and powered by a standard power supply 30. The light output from the lamp is preferably collimated.

The transmitted light beam, after passing through the fluid analysis unit 14, is directed through a shutter 32. The shutter is used to block the light emitted from the light source, so that dark-current measurements can be made during the calibration step. The transmitted light is then received by a camera lens 34 and passed through the monochromator 18 to the detector 20. The entrance and exit slits (not shown) of the monochromator enable the detector to detect single frequency radiation and, the size of the slits, together with the diode spacing of the diode array detector, defines the wavelength resolution of the spectrophotometer.

The lamp housing 28 also preferably includes photometric filters (not shown) contained in a filter holder 36 to vary the intensity of light reaching the detector. This enables the detector to operate in its optimum condition, without saturation by high intensity light, or lack of resolution with low intensity light, which enables the detectors to see virtually in the dark. The detector 20 is preferably a standard photodiode array detector which comprises a high sensitivity photodiode array connected to a low noise amplifier. The transmitted light is sent to the detector for spectral measurement and the detector signal is then fed via fiber optic RS-232 cables 25 from the diode array controller 24 to a computer 16 for spectral analysis and L*, a*, b* color value computation, which constitutes the color measurement.

The apparatus may also contain an integrating sphere (not shown) integral with the light source for diffuse illumination of the sample, in the case where the measured fluid possesses more than negligible light scattering capability. Said integrating sphere may also possess an automatically controlled black trap and white reflector sliding mechanism (not shown) for illuminating the sample with either solely diffuse light or diffuse and specular light for analysis of samples possessing scatterers.

Fluid analysis unit 14, comprises a fluid control unit 38, as will be later described, which supplies a continuous flow of fluid under investigation or reference fluid to a flow through fluid analysis cell 40.

Figure 3A:
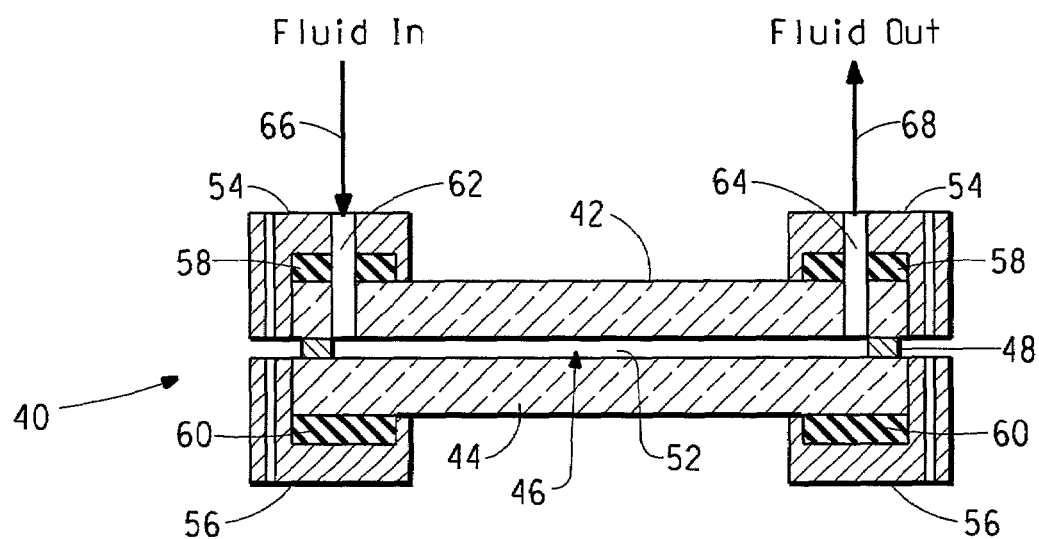
FIG. 3A is a side view of the flow-through fluid analysis cell used in the apparatus of FIG. 1.
Figure 3B:
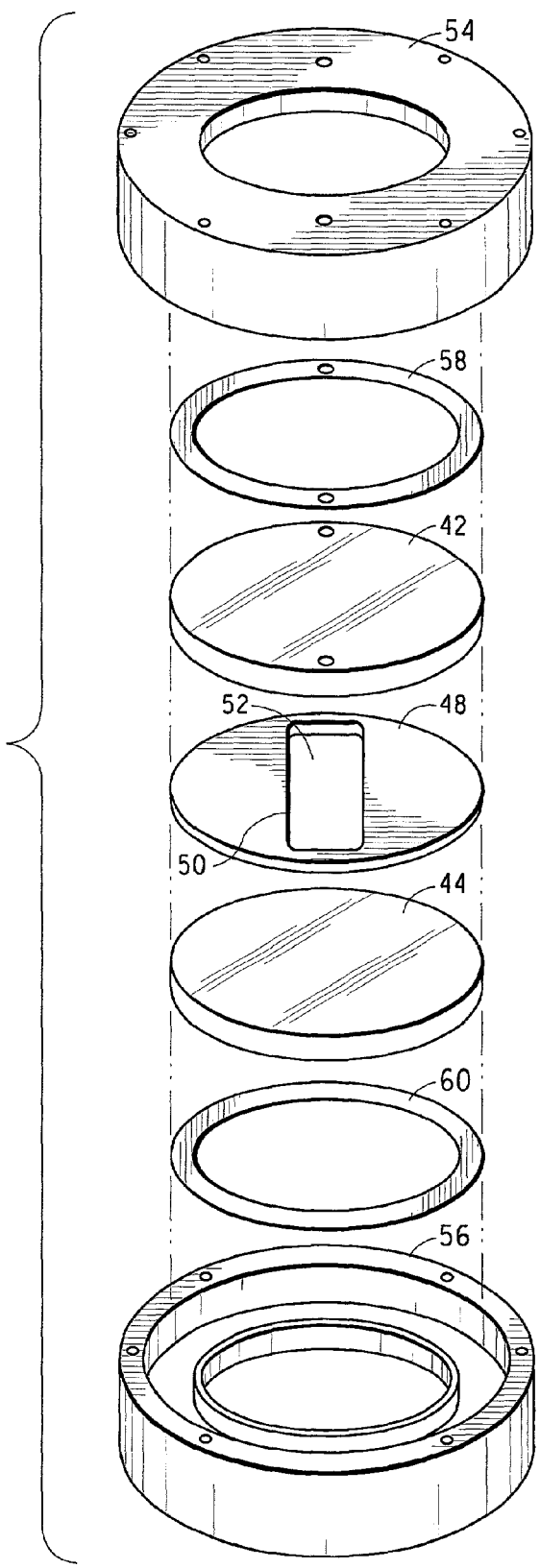
FIG. 3B is an isometric view of the flow-through fluid analysis cell of FIG. 3A.

Referring now to FIGS. 3A and 3B, the fluid analysis cell 40 is designed to provide a fluid stream of uniform color so that accurate color measurements can be made. The cell 40 comprises a vessel containing upper and lower viewing widows 42 and 44, respectively, preferably cylindrical windows, that are fixedly mounted to each other and close the opposite ends of the vessel. The viewing widows are made of materials that are transparent to visible light, for example such as borosilicate glass, quartz, or sapphire, and allow for light transmission through the cell. Between the windows is a cavity which forms a fluid analysis chamber 46. The fluid analysis chamber 46 is formed by having a spacer member 48, such as a brass shim, inserted between the viewing windows.

The spacer member 48 is provided with an rectangular cavity 50 which creates a fluid flow channel 52 therein. The thickness of the spacer determines the cell pathlength, and may be of any size, although for practical reasons (because of absorbance of the samples being measured) a thickness between 1 and 10 mils (0.001 to 0.010 inch) is usually chosen. The upper and lower viewing windows and shim 48 are fixedly held in place by upper and lower flanges 54 and 56 bolted together to hold the entire assembly. Elastomeric gaskets 58 and 60 are inserted respectively between upper flange 54 and upper window 42 and between lower flange 56 and lower window 44 to seal the assembly. The flanges 54 and 56 are similarly provided with flow conduits 62 and 64, respectively, to enable fluid communication with the flow channel 52 and provide fluid inlet and outlet channels 66 and 68 to the cell. The fluid inlet and outlet channel are usually threaded to receive standard fittings (not shown) to interface with inlet and outlet pipes (not shown).

The components that are used to form the transmission cell 40 should be made of materials which are non-reactive with the fluid that is being passed through the apparatus. Typically the structural components are made of brass or stainless steel and the viewing windows are made of borosilicate glass, quartz, or sapphire, as indicated above. The viewing windows may also be coated with a fluorocarbon polymer to prevent fluid residue build-up on the cell.

The transmission cell 40 of the present invention may be characterized as a zero bypass cell, which means that all fluid entering is exposed to the viewing windows. Zero bypass enables sample to flow through the cell at a uniform shear to provide a constant interface that can be measured and at a sufficient velocity to prevent a build-up on the cell window. Flow through the cell should also be laminar which prevents settling or flocculation of any pigment suspended in the fluid. Laminar flow also provides a sample of uniform color in the viewing area to insure uniform color measurements. The zero bypass cell also guarantees that all of the fluid will cross the optical view path so as to give a true sample of the fluid.

Another feature of the cell used in the present invention is that the pathlength of light through the sample is fixed but can be set manually by a change in the shim spacer in the cell. Thus one always knows what the pathlength is and does not have to worry about pathlength control and errors that can result during measurement. Pathlength of the light through the sample is set small enough to allow sufficient light throughput to be accurately measured by the instrument detectors, yet large enough to avoid saturation of the detectors. This enables measurement of transparent as well as opaque fluids. Additionally, the pathlength should be set so that the appropriate lightness of the sample is attained, such that possible colorant modification, or shading, in the wet state corresponds to that in the dry. As indicated above, the pathlength is typically set between 1 and 10 mils. However, for some optically dense dispersions, dilution may be necessary to obtain full spectral information.

To maintain proper pathlength control, temperature of the measurement cell and the liquid within the cell is preferably held to a narrow enough range (e.g., plus or minus 5° C.) such that thermal expansion does not change the effective pathlength and such that the standard and sample readings are comparable. Temperature control in the present invention is preferably provided by a thermoelectric cooler 70 disposed in the housing 10 next to the cell to insure a constant temperature of fluid passing through the cell, as shown in FIG. 2. The test sample and liquid standard should also be measured at the same temperature within this range to insure uniformity.

The fluid flow control unit, or sample system, 38 is also shown in FIG. 2. Generally any type of control unit can be provided which pumps fluid at a uniform velocity into the apparatus through the inlet and into the fluid chamber formed by the spacer and across the viewing windows and out through the outlet. Color measurements can then be made through the windows by transmittance as a sample volume of fluid is passing through the cell.

In the preferred embodiment as shown, the fluid control unit or sample system 38 provides for injection of sample into the cell through a sample injection port 72 and for sample line and cell cleanout. The fluid control unit itself is preferably controlled by the same computer 16 which controls the optical unit which gathers the spectral measurements. This can be accomplished via an RS-232 serial link 74 through an input/output (I/O) rack 76 (e.g. a programmable logic controller or PLC), which in turn triggers solenoid valves 78, releasing air to the pneumatic components (not shown) of the sample system. Additional I/O rack modules 80 are preferably interfaced to pumps, temperature and pressure sensors, and purge air supply (all not shown).

Preferably, the system possesses an explosion-proof NEMA 4 enclosure 10 for all electrical and electronic components as well as the light source. Said enclosure is also purged with air to a pressure super-ambient with respect to the exterior environment to prevent buildup of an explosive atmosphere, possibly present exterior to the enclosure, within the enclosure. The purge air system consists of an air purge unit 82 plus a pressure vessel air tank 84 for containment of an emergency air purge in event of system failure as shown in FIGS. 1 and 2.

The air purge unit contains an electronic control unit 86 which controls all electrical power to the system, and has sensors capable of detecting a breach of the cabinet seal, whereupon an emergency electrical shutdown of the system is effected, along with a controlled depressurization of the emergency air tank and venting of the air via a conduit (not shown) through the light source housing 28, thus preventing any possible explosive vapors from coming in contact with the light source until it is cooled down. Additionally, the electronic control unit will not allow startup of the system until a timed fast purge of the enclosure via a conduit (not shown) is first accomplished. Moreover, a pressure sensor (not shown) on the emergency air tank acts as a trigger for startup of the light source, disabling the same until the air tank is at full pressure.

Before a fluid sample may be measured, a reference reading is taken by first injecting solvent into the sample cell 40 via a standard menu-driven computer program. The program controls the sample system's 38 pneumatic components (not shown) by signaling the I/O rack 76 via RS-232 serial link 74 to operate the appropriate component via solenoid valves 78 in the cabinet 10. When each task is completed (by time or sequence), the pneumatic components return to their default positions.

To take a reference spectrum, the computer-controlled sample system's pneumatic components (not shown) are set such that solvent from the solvent reservoir (not shown) is directed by a pump 88 into the sample cell 40. A dark current spectrum is taken by blocking the light with the air-operated shutter 32 inside the cabinet (this happens each time a spectrum is collected for both reference and sample measurements). Once this has been recorded by the program, the shutter is opened and the program reads and records the light spectrum from the diode array 20, subtracts the dark current spectrum from reference and stores the result in raw format as the reference spectrum.

When a fluid sample is to be analyzed, a sample is delivered to the sample system 38, either manually or automatically. The sample system is set to air-drive the sample through the sample cell 40. The computer program reads and records the light spectrum from the diode array 20 and converts it into transmission by comparing it with the solvent reference spectrum as well as the dark current reading from the diode array. L*, a*, and b* are then calculated via standard equations.

The color technology used for spectral analysis, calculation of the L*, a*, b* color values of the fluid being tested therefrom, and making color comparisons to a standard is well known and fully described in Falcoff et al, U.S. Pat. No. 4,403,866 issued Sep. 13, 1983, hereby incorporated by reference.

To clean the sample system 38, the system is set in such a way that solvent is directed from the reservoir (not shown) through the sample system first, to effect cleaning there, and then through the cell 40, wherein the high shear of the solvent flow cleans the faces of the cell windows. All pneumatic components then return to their default positions when the operation is complete, and the system is ready for the next sample.

The apparatus can be used in a variety of chemical processes in which color of the resulting product is measured. It is preferably used in a paint, pigment dispersion, inkjet ink, printing ink, or tint manufacturing process. The apparatus of this invention can be positioned at a remote location from the manufacturing process for either at-line or off-line testing, or can be and preferably is connected to the production unit for on-line color testing of the wet fluid as it is being made. Allowing the fluid to flow through the cell directly from the processing unit allows for on-line or continuous testing and enables fully automated batch or continuous manufacture of the fluid. The total cycle time of the apparatus as shown in FIG. 1 is a few minutes as opposed to hours using conventional equipment. Moreover, it has been found that in making color measurements using this apparatus, there is a good correlation between the color properties of the wet fluid and dry fluid, which enables visually accurate color matches to be achieved.

A variation of this invention is to use a colorimeter in place of the spectrophotometer.

What is claimed is:

1. An apparatus for measuring the color properties of a fluid, comprising:
   a fluid analysis cell having a cavity therein for measuring light transmittance of a sample over the visible spectrum, from 400 to 700 nm;
   an upper and lower light transmitting window enclosing opposite ends of the cavity;
   a spacer member fixedly positioned in said cavity between said upper and lower viewing windows providing a fluid chamber of fixed pathlength where fluid flows between said windows; and
   inlet and outlet channels connected in fluid communication with said fluid chamber to enable fluid to flow into and out of said fluid chambers,
   wherein the fluid analysis has zero by-pass so that fluid entering the cell is exposed to the viewing windows.

2. The apparatus of claim 1 in which a visible light source and a spectrophotometer are associated with the fluid analysis cell for directing light to the fluid analysis cell and detecting light therefrom, respectively, to measure color parameters of the fluid passing through the viewing windows by transmittance.

3. The apparatus of claim 2 in which the spectrophotometer is a single beam spectrophotometer and the light source is a tungsten halogen lamp.

4. The apparatus of claim 2 which further includes:
   a purged explosion-proof enclosure for containing all electrical/electronic components, as well as the light source for the instrument;
   an automatic pneumatically-controlled sample system for delivery of the sample to the fluid analysis chamber; and,
   an explosion-proof gear pump for high pressure delivery of cleaning solvent to the fluid analysis chamber for rapid cleaning of said chamber.

5. The apparatus of claim 2 in which a camera lens interfaces with the spectrophotometer to gather light from diffuse as well as specular directions.

6. The apparatus of claim 2 in which the light source also preferably includes photometric filters to vary the intensity of light reaching the detector, allowing the detector to operate in its optimum condition, without saturation by high intensity light, or lack of resolution with low intensity light.

7. The apparatus of claim 2 in which the flow of fluid through the fluid analysis chamber is unidirectional and laminar at a uniform shear.

8. The apparatus of claim 2 in which the windows are of borosilicate glass and the spacer member is of brass.

9. The apparatus of claim 2 in which the fluid analysis cell is cylindrical.

10. The apparatus of claim 2 in which an integrating sphere integral with the light source for diffuse illumination of the sample is juxtaposed between the light source and the cell for diffuse as well as specular illumination, in the case where the measured fluid possesses more than negligible light scattering capability.

11. The apparatus of claim 10 which also includes a controlled black trap and white reflector sliding mechanism for illuminating the sample with either solely diffuse light or diffuse and specular light for analysis of samples possessing scatterers.

12. The apparatus of claim 1 wherein the pathlength is set between 1 and 10 mils.

13. The apparatus of claim 2 wherein the pathlength is set between 1 and 10 mils.

* * * * *